(12) United States Patent
Muntermann

(10) Patent No.: US 6,719,756 B1
(45) Date of Patent: Apr. 13, 2004

(54) ELECTRODE CATHETER WITH REDUCED NOISE ACTIVITY AS WELL AS A RELATED PROCESSING METHOD FOR THE ELECTRODE SURFACE

(76) Inventor: Axel Muntermann, Gotenweg 51, D-35578 Wetzlar (DE)

( * ) Notice: Subject to any disclaimer, the term of this patent is extended or adjusted under 35 U.S.C. 154(b) by 0 days.

(21) Appl. No.: 10/049,932
(22) PCT Filed: Aug. 16, 2000
(86) PCT No.: PCT/EP00/07943
§ 371 (c)(1), (2), (4) Date: Aug. 7, 2002
(87) PCT Pub. No.: WO01/12259
PCT Pub. Date: Feb. 22, 2001

(30) Foreign Application Priority Data

Aug. 17, 1999 (DE) ......................... 199 38 558

(51) Int. Cl.⁷ .............................. A61B 18/18
(52) U.S. Cl. ........................ 606/41; 600/374
(58) Field of Search ............... 606/41, 45, 46, 606/48–52; 600/374

(56) References Cited

U.S. PATENT DOCUMENTS

| 4,653,500 A | | 3/1987 | Osada et al. |
| 4,896,671 A | * | 1/1990 | Cunningham et al. ....... 600/374 |
| 5,423,882 A | * | 6/1995 | Jackman et al. ............ 607/122 |
| 5,713,895 A | * | 2/1998 | Lontine et al. ............... 606/41 |
| 5,810,764 A | | 9/1998 | Eggers et al. |
| 5,991,650 A | * | 11/1999 | Swanson et al. ............ 600/374 |

FOREIGN PATENT DOCUMENTS

DE 197 40 976 A1 9/1997

* cited by examiner

Primary Examiner—Michael Peffley (57) ABSTRACT

A catheter for the ablation of biological, in particular of animal or human, tissue, preferably for the ablation of human myocardial tissue, has at least one ablation or mapping electrode to permit the recording of ECG signals during catheter ablation and, in particular, to improve the quality of the recorded ECG signals to such an extent as to permit medical statements with reference to cardiac action. The at least one ablation or mapping electrode has a reduced number of electrical interference centers. Furthermore, the invention provides methods and apparatuses with the aid of which conventional catheters can be treated in such a way that these interference centers are reduced.

18 Claims, 10 Drawing Sheets

ELECTRODE CATHETER WITH REDUCED NOISE ACTIVITY AS WELL AS A RELATED PROCESSING METHOD FOR THE ELECTRODE SURFACE

CROSS REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Technical Field of the Invention

The invention relates to, a catheter for the ablation of biological, in particular of animal or human, tissue, including ablation of human myocardial tissue, a method for treating catheters, and an apparatus for carrying out the treatment of catheters.

2. Description of Related Art

One of the main aims in the catheter ablation of myocardial tissue is to interrupt, by lesions of the upper layers of the heart tissue, regions of the conduction system that can have a negative effect on the cardiac action. The success of a treatment depends, however, very substantially on whether the correct depth of lesion was achieved during the ablation. In this case, correct depth of lesion means in essence that the undesired regions disrupting the conduction system are removed, but that no further-reaching injuries are introduced. It is evident that with an excessively small depth of lesion the success of treatment is endangered, whereas in some circumstances an excessively large depth produces very many relatively severe side effects. Since there are vessel walls running in the heart which may not be unnecessarily damaged, and also the tissue to be ablated is frequently only of a limited thickness, in the event of excessively large depths of the lesions it is even possible for lethal accidents to occur because of severed heart walls or heart vessels. An attempt has therefore been made in the case of conventional ablation methods to estimate the optimum depth of lesion by the synchronous recording of ECG signals on the occurrence of success in treatment. However, in this case the irradiated high-frequency energy was exceptionally detrimental to the recording of these signals, and an attempt was undertaken to mitigate such influences by means of appropriate electrical or electronic filters in the downstream equipment. However these attempts had only limited success, or none. Producing the irradiated power led to extremely long treatment times which are in the range of several hours and in this case both subject the patient to substantial stress and are unable to reliably prevent slippage of the ablation catheter. Furthermore, lesion is no longer possible starting from a specific power, since the temperature generated no longer suffices for tissue coagulation.

BRIEF SUMMARY OF THE INVENTION

It is therefore the object of the invention to permit the recording of ECG signals during catheter ablation and, in particular, to improve the quality of the recorded ECG signals to such an extent as to permit medical statements with reference to cardiac action.

This object is achieved by the invention in an exceptionally surprising way with the aid of a catheter for the ablation of biological, in particular of animal or human, tissue, including ablation of human myocardial tissue, said catheter comprising at least one ablation or mapping electrode, wherein the at least one ablation or mapping electrode has a reduced number of electrical interference centers which generate microscopic electric field strength differences or microscopically different reaction capabilities and, wherein the at least one ablation or mapping electrode has a treated surface with a microscopically smoothed surface structure whose microscopic edges or tips have a radius of curvature of more than 10 nm. This objective is also achieved by a method for producing a catheter with improved electrical properties, the method comprising the following steps: providing a catheter which comprises at least one ablation or mapping electrode,-and treating the at least one ablation or mapping electrode its surface, wherein the surface of the at least one ablation or mapping electrode is smoothed at least until structures which have a diameter of less than 10 $\mu$m are reduced in number.

The inventor surprisingly followed a completely different path than has previously been the case in the known prior art.

Instead of subjecting the recording equipment to change or an attempt at improvement, the cause of interference in the recording of the ECG signals were reduced or even completely eliminated.

The inventor was the first to find out that the cause of the electrical interference in the ECG recording during simultaneous irradiation of high-frequency energy essentially resides not in the leads to and from the catheter electrodes, not in the electronic recording devices and, in particular, not in their input filters, but in electrical interference centers in the region of the surface of the ablation or mapping electrodes.

This finding was all the more surprising since every investigated ablation catheter with platinum electrodes exhibited such electrical interference centers and, after their reduction or removal, was virtually or completely free from the undesired interference previously described.

In accordance with the invention, in the case of a catheter for the ablation of biological, in particular animal or human, tissue, preferably for the ablation of human myocardial tissue, having at least one ablation or mapping electrode, this at least one ablation or mapping electrode has a reduced number of electrical interference centers. For example, this improves the disturbed ECG recordings illustrated in FIGS. 4, 5 and 7 in such a way that the signals illustrated in FIG. 6 can be obtained.

In a particularly advantageous way, the electrical interference centers which generate electric signals during the output of high-frequency energy to the at least one ablation or mapping electrode and which are essentially arranged on surface regions of the at least one ablation or mapping electrode are reduced in their number, areal extent and/or electrical effect. This results in a removal or electrical deactivation of the influence of these interference centers.

A particularly effective method for achieving the above successes consists in that the at least one ablation or mapping electrode has a mechanically treated surface, since electrical interference centers in the surface can be removed and/or greatly reduced in their effect thereby.

The at least one ablation or mapping electrode preferably has a mechanically treated surface which is treated using a method which smoothes the surface. Prior surface treatments, for example in the case of platinum-iridium catheters, have aimed at enlarging the surface, that is to say precisely not to smooth the surface but to create structures that are rough, having a surface that is larger approximately by the factor 1000; however, the invention proceeds, with surprising success, precisely along the opposite path.

In a particularly preferred and advantageous embodiment, it is provided that the at least one ablation or mapping electrode comprises a noble metal, in particular platinum, whose surface is smoothed, in particular lapped or polished. It has proved in this case to be particularly effective to use a grinding or polishing agent which contains calcium carbonate.

Alternatively or in addition, it can be provided that the ablation or mapping electrode surface is rolled with a smooth roller.

It was frequently to be observed after the above-described treatment that structures of the surface of the at least one ablation or mapping electrode have a rounded surface structure whose edges have a radius of more than approximately 500 nm, preferably of more than 100 nm, but at least more than 10 nm, and it is suspected that these surface changes already cause at least a portion of the reduction in the electrical interference centers or their effects.

It is assumed, moreover, that, owing to the mechanical treatment, peaks in the electric field strength that are present on the surface, for example owing to grain boundaries in the metal, present in crystalline form, are also smoothed or compensated, and that after the treatment according to the invention microscopic differences in the electric field strength or microscopically differing reaction capabilities at the electrode surface are also mitigated or compensated. This mitigates the phenomena occurring during the output of HF energy, which are ascribed without limitation of the generality or the scope of the invention to locally differing ionic mobility, the point being that there is no longer any "running on" by ions or polar molecules which are moved to a greater or lesser extent by different field strengths which would cause the formation of interfering electric potentials or field strengths that are superimposed on the ECG signal as interfering signal. The ions which now move virtually identically at all locations on the surface of the ablation or mapping electrode no longer generate local potential or field strength differences and also no longer disturb the ECG recording.

It is therefore assumed that, when the catheter advantageously comprises a platinum ablation or mapping electrode, the surface of the at least one ablation or mapping electrode is coated or provided at least partially with elementary platinum. It is, however, also within the scope of the invention for such an atomic, essentially non-crystalline or amorphous coating also to be produced, for example, using techniques for coating or plating, for example grinding thin, preferably amorphous films.

It then results in an advantageous way that the surface of the at least one ablation or mapping electrode comprises regions with deposited metal present essentially in an amorphous manner or atomically.

BRIEF DESCRIPTION OF THE SEVERAL VIEWS OF THE DRAWINGS

The invention is explained in more detail below with the aid of preferred embodiments and with reference to the attached drawings, in which.

DETAILED DESCRIPTION OF THE INVENTION

The invention is described below in more detail and with reference to the attached drawings.

Figure 1:
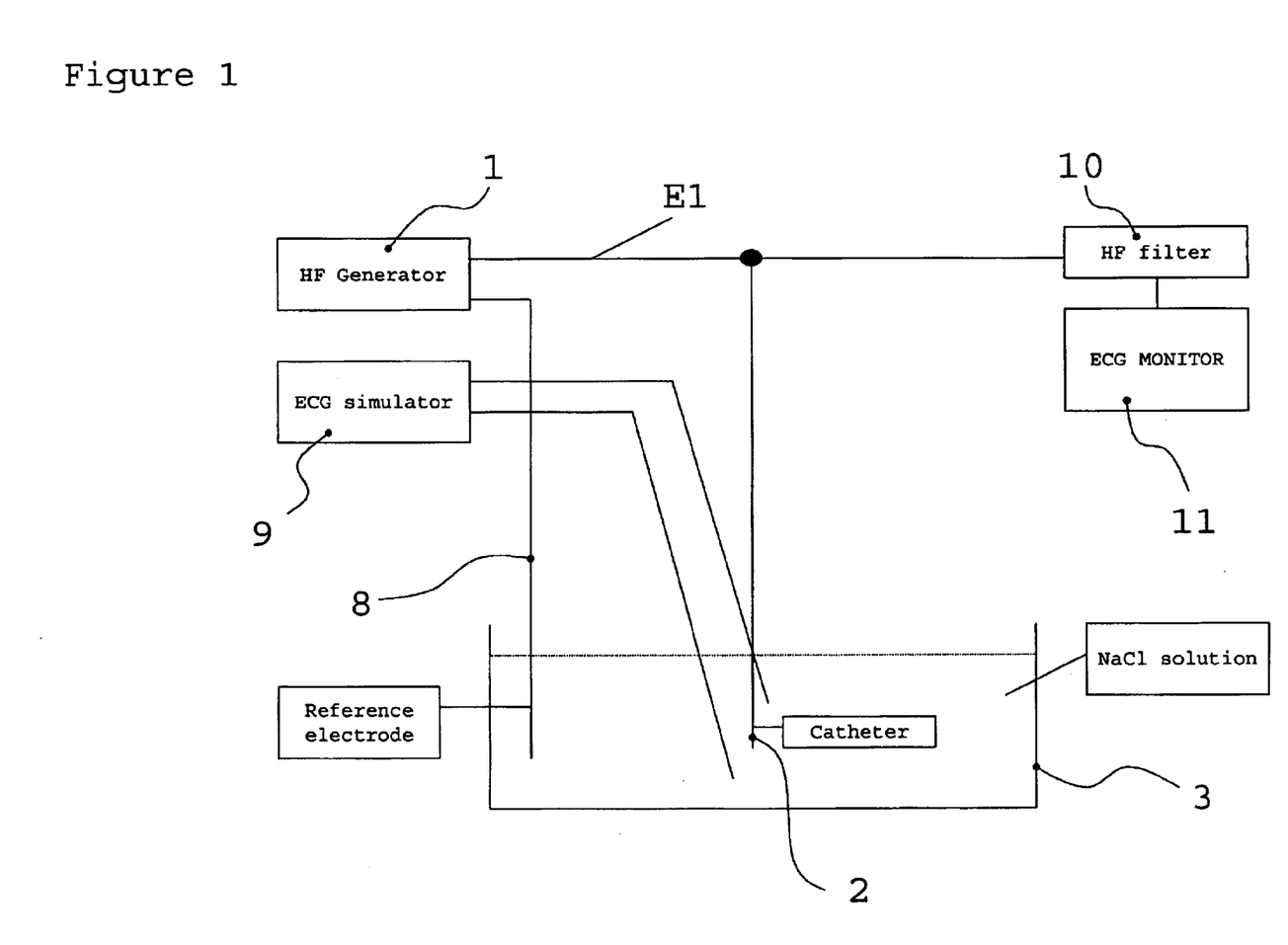
FIG. 1 shows a schematic illustration of an apparatus for measuring simulated ECG signals with and without irradiated high-frequency energy.

Reference is firstly made to FIG. 1 from which there may be gathered a schematic illustration of an apparatus for measuring simulated ECG signals with and without irradiated high-frequency energy, which has been used both for recording the disturbed ECG signals with non-treated catheters and for recording the improved signals with treated catheters.

FIG. 1 shows a high-frequency generator 1, which is connected to a catheter 2, and a vessel 3 filled with electrolyte.

In the example from FIG. 1, the catheter 2 is provided with at least one ablation or mapping electrode, which is connected to the generator 1 via a supply lead E1, and with one or more further electrode(s), which is/are connected to the generator 1 via one or more further supply leads E2. The further electrodes can be mapping electrodes or one or more ablation electrodes.

The vessel 6 was filled with a physiological NaCl solution and the catheter 2 was arranged therein in such a way that its ablation or mapping electrode was completely wetted by the NaCl solution. The catheter 2 was also connected to the conventional high-frequency generator 7 in such a way that the ablation electrode of the catheter 2 was fed with the high-frequency energy values typical of ablation.

The HF field was generated by the HF generator 1 between the ablation or mapping electrode of the catheter 2 and a reference electrode 8, and in this way represented to a very good approximation a situation such as also obtains in the human heart, for example.

An ECG simulator 9 was used to generate voltage signals which corresponded to a very good approximation to the electric voltages output by the human heart, both in terms of level and of their time profile.

The catheter 2 was also connected to a high-frequency filter 10 which filtered out the high-frequency signal components fed in by the HF generator 1. Such filter arrangements are well known to the person skilled in the art and can correspond, for example, to the input filters used in the QuadraPulse unit from AD Electronic.

The ECG signal obtained, as tapped from the catheter, in particular from its mapping electrode, or even its ablation electrode, was then fed to an ECG monitor 11 such as is marketed, for example, by Physiocontrol under the designation of LIFEPAK 10 or by Bard as EP-Laborsystem.

The catheter 2 was measured after being treated and it emerged that the at least one ablation or mapping electrode with a mechanically treated surface has fewer electrical interference centers.

In accordance with the invention, the mechanically treated surface was treated using a method which smoothes the surface and in which structures of the surface of the at least one ablation or mapping electrode have a rounded surface structure whose edges have a radius of more than approximately 500 nm, preferably of more than 100 nm but at least more than 10 nm.

This rounding could be produced, for example, by virtue of the fact that the ablation or mapping electrode surface was lapped or polished with a grinding or polishing agent which contains calcium carbonate. In general, according to the invention treatment is performed with a soft grinding or polishing agent which comprises a carbonate, preferably an alkali or alkaline earth carbonate. It turned out surprisingly that polishing agents used in oral hygiene, for example toothpaste or tooth polishing and cleaning preparations are well suited in many cases.

As an alternative or in addition, the ablation or mapping electrode surface was rolled with a smooth roller in order thereby likewise to achieve the desired microscopic smoothing.

Furthermore, alternatively or in addition, the mechanical treatment comprises the application of a film with a smooth surface, in particular the grinding of the film with a smooth surface onto the at least one ablation or mapping electrode such that the smooth film surface comes to interact with the external surroundings.

Suitable as catheters for carrying out the invention are essentially all known ablation catheters, in particular catheters with platinum electrodes, and the following specified catheters, for example, were used successfully in the investigations of the inventor:

1. BARD SideWinder Catheter S/N: 17009000
2. BARD SideWinder Catheter S/N: 1300013000
3. Cordis Webster Catheter Internal S/N: CW1
4. Cardiac Pathways Catheter S/N: G709313
5. Biotronic Catheter: AlCath Twin (non-ablation catheter, fractal Pt/Ir surface)
6. BARD Stinger Distal Tip ablation catheter 4 mm Tip
7. BARD Stinger Distal Tip ablation catheter 8 mm Tip
8. Biotronic Catheter AlFractal, Distal Tip
9. Ablation catheter (fractal Pt/Ir surface)

The results obtained are explained in more detail below with reference to FIGS. 2 to 10.

Figure 2:
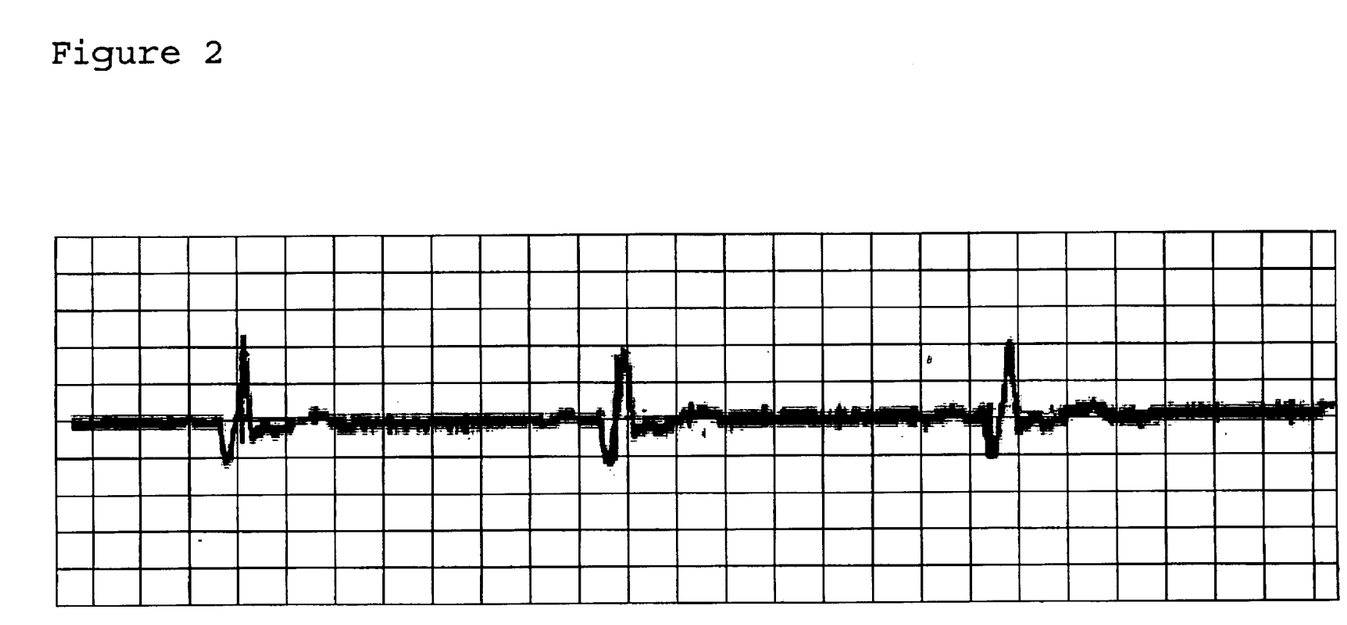
FIG. 2 shows a simulated ECG signal, as mapping signal, before electrode treatment without applied high-frequency energy.
Figure 3:
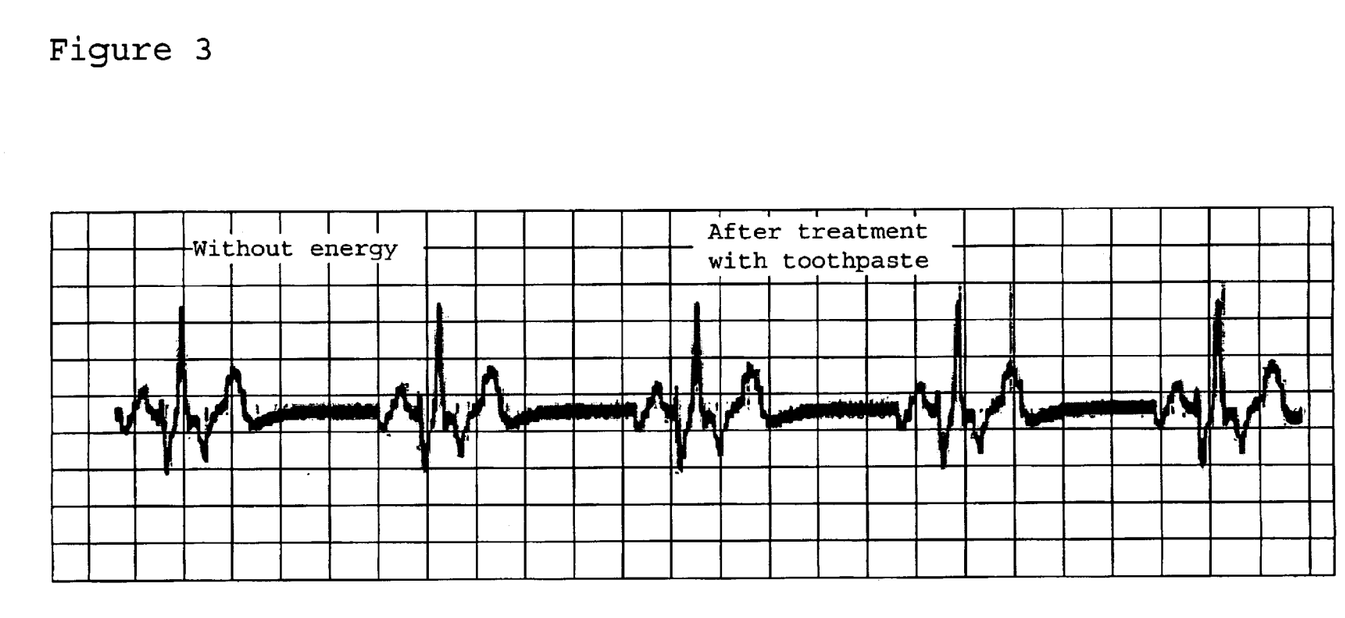
FIG. 3 shows a simulated ECG signal, as mapping signal, after electrode treatment without applied high-frequency energy.

As long as no high-frequency energy or high-frequency voltage was fed to the catheter electrodes, FIGS. 2 and 3 prove that the recording of the ECG signals could be undertaken virtually without interference.

Figure 4:
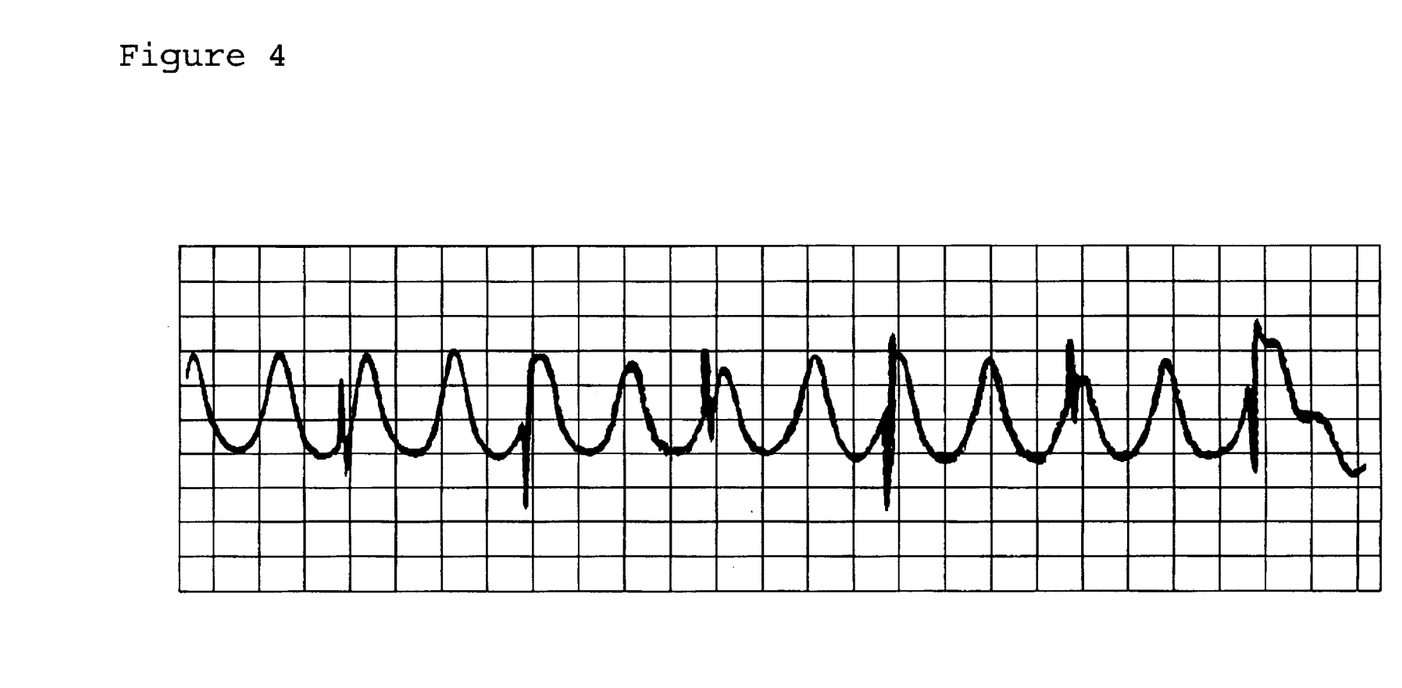
FIG. 4 shows interference in the simulated ECG signal in the case of fast, non-pulsed power regulation of the output high-frequency energy for a non-treated ablation catheter.

However, if the level of the high-frequency voltage or the amount of irradiated high-frequency energy is regulated during the ECG recording, as is the case during a real ablation procedure on the patient, voltages arise which vary virtually linearly in proportion to the irradiated energy and are illustrated, for example, in FIG. 4.

Regulation of the output energy in the course of a power regulation of the irradiated high-frequency energy therefore always leads to superimposition of interference signals on the ECG signals, which renders it impossible, as a rule, for the physician to make a statement on the success of treatment or the current condition of the heart.

Figure 5:
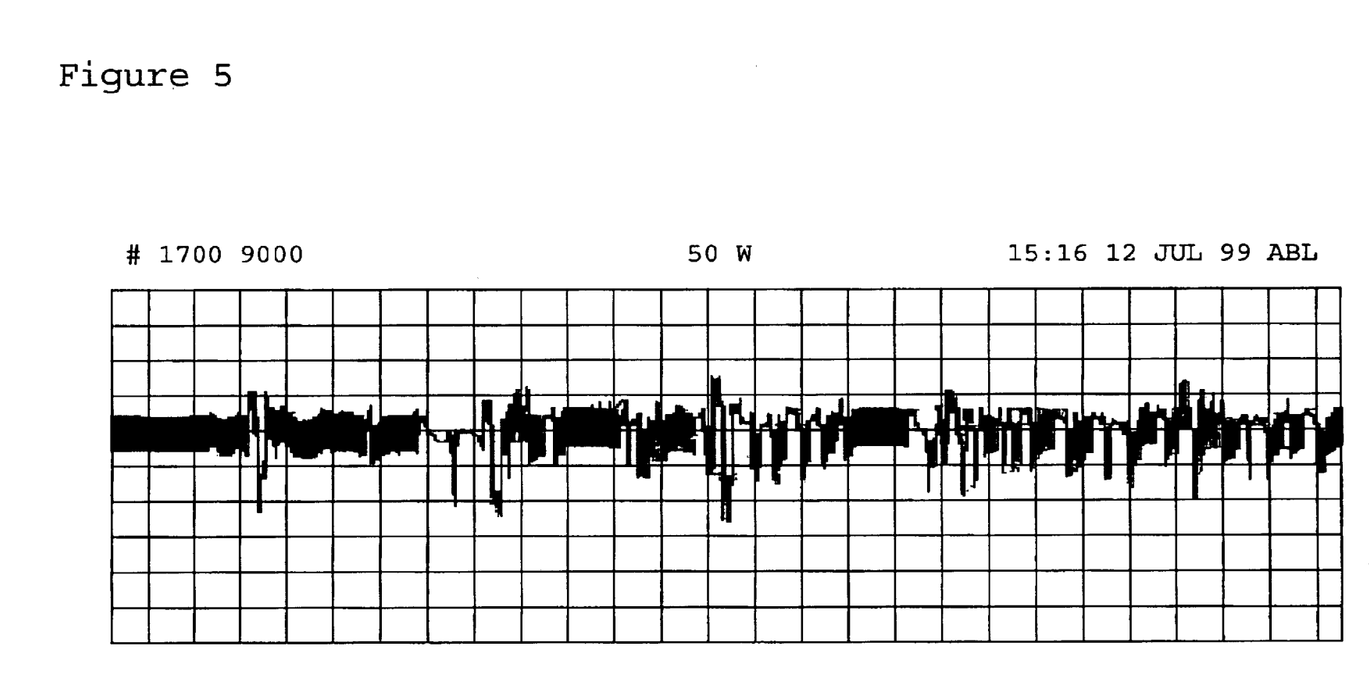
FIG. 5 shows interference in the simulated ECG signal in the case of fast, pulsed power regulation of the output high-frequency energy for a non-treated, quadrupole ablation catheter with cylindrical platinum ablation electrodes each 4 mm long.
Figure 6:
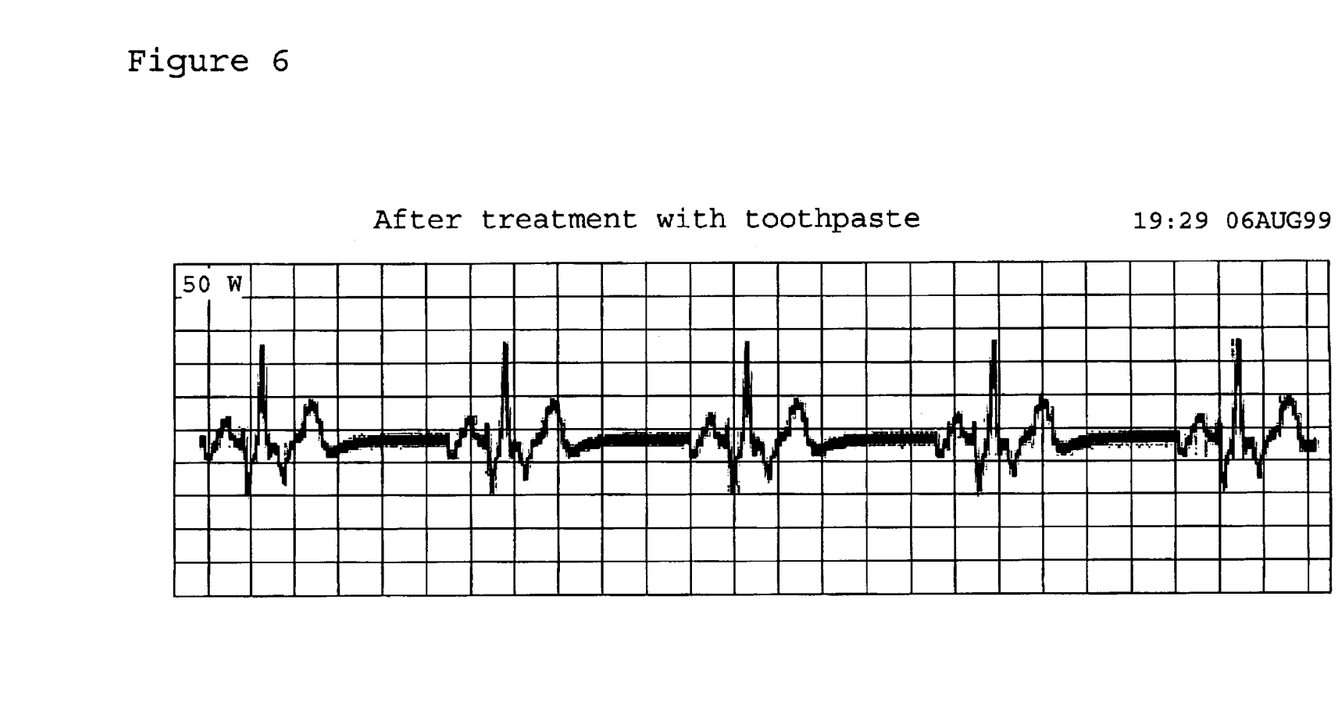
FIG. 6 shows a simulated ECG signal in the case of output high-frequency energy for the quadrupole ablation catheter with cylindrical platinum ablation electrodes, each 4 mm long, after its treatment.
Figure 7:
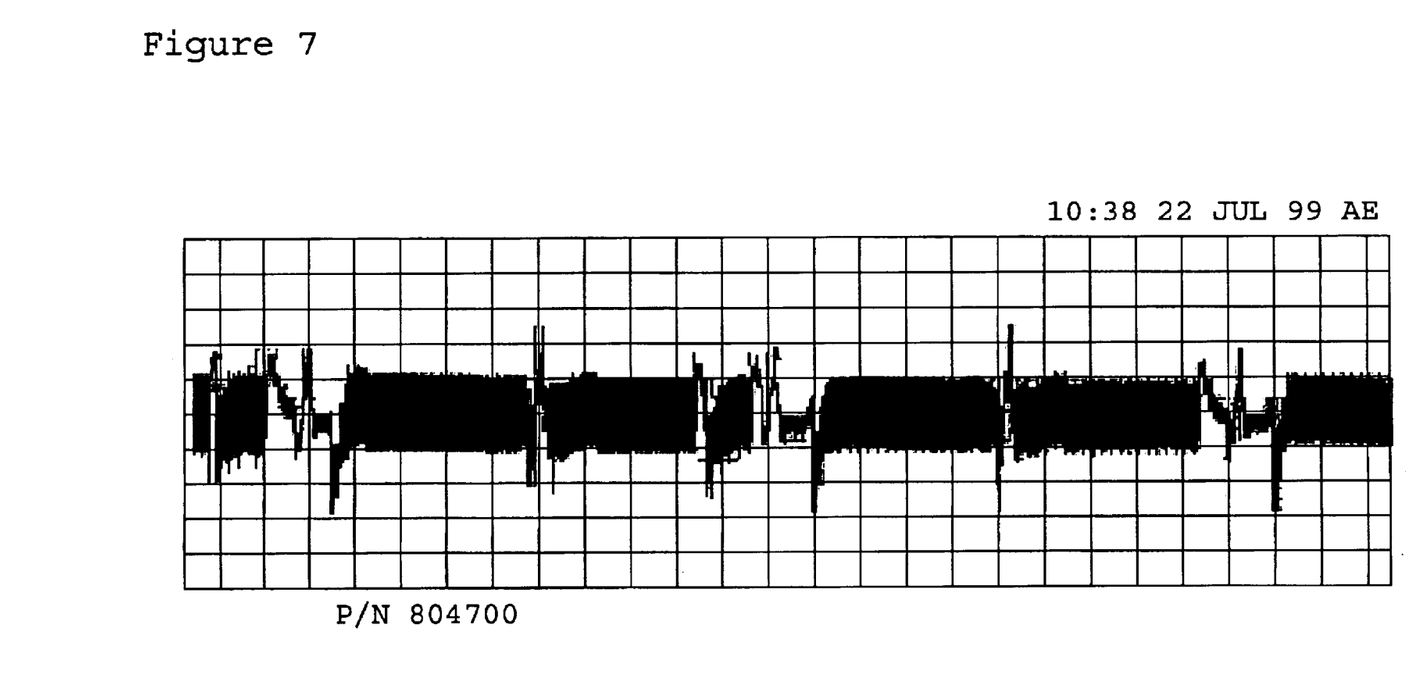
FIG. 7 shows interference in the simulated ECG signal in the case of fast, pulsed power regulation of the output high-frequency energy for a non-treated ablation catheter with a cylindrical platinum ablation electrode 4 mm long, and three further mapping electrodes.

Even more difficult is the situation in the case of pulsed power regulation, as illustrated in FIGS. 5 and 7, in which figures it is virtually no longer possible to detect any components of the ECG signal at all.

The high-frequency power irradiated in the case of these experiments was from approximately 1 to 50 W, as is entirely normal for high-frequency catheter ablation in human hearts.

However, if an ablation catheter was treated in the way described above, it was possible in conjunction with the same experimental set-up to reduce the superimposed interference to a great extent, in any case by a factor of more than ten, as is illustrated, for example, in FIG. 3.

The experimental set-up, identical per se in each case, which differed only in whether the catheter was used directly as marketed by the respective manufacturer or whether it was treated in the way according to the invention, proves the great success of the present invention unambiguously.

The catheters according to the invention therefore have on their electrode surfaces fewer electric or electronic interference centers which can generate the superimposed signals. The measure of the reduction in interference is therefore a measure of the presence or the reduced or diminished presence of such interference centers.

It is assumed without limitation of generality and without limiting the invention that the generation of such signals superimposed on the ECG signal is due to local adhesion sites or local extremes in the electric potentials or field strengths occurring on the surface of the catheter, at which ions or molecules of dipole moment can be bound with differing strength or moved, and can then, upon application of the HF voltage or HF energy, generate, because of the different mobility as against the dissolved ions, a voltage signal which is superimposed on the ECG signal.

Figure 8:
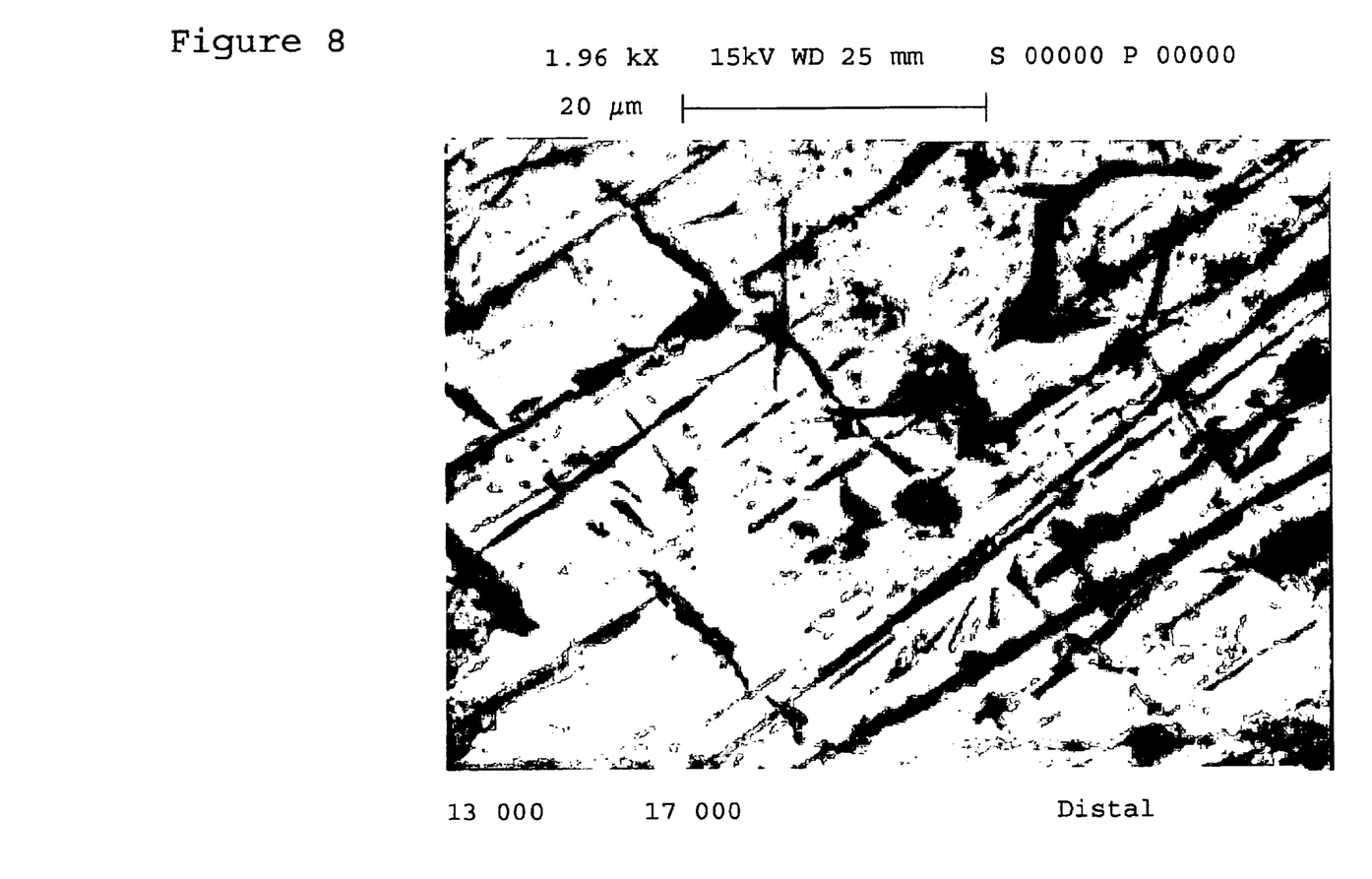
FIG. 8 shows an electron microscope photograph of the platinum surface of the ablation electrode of a non-treated ablation catheter with 1 960-fold magnification.
Figure 9:
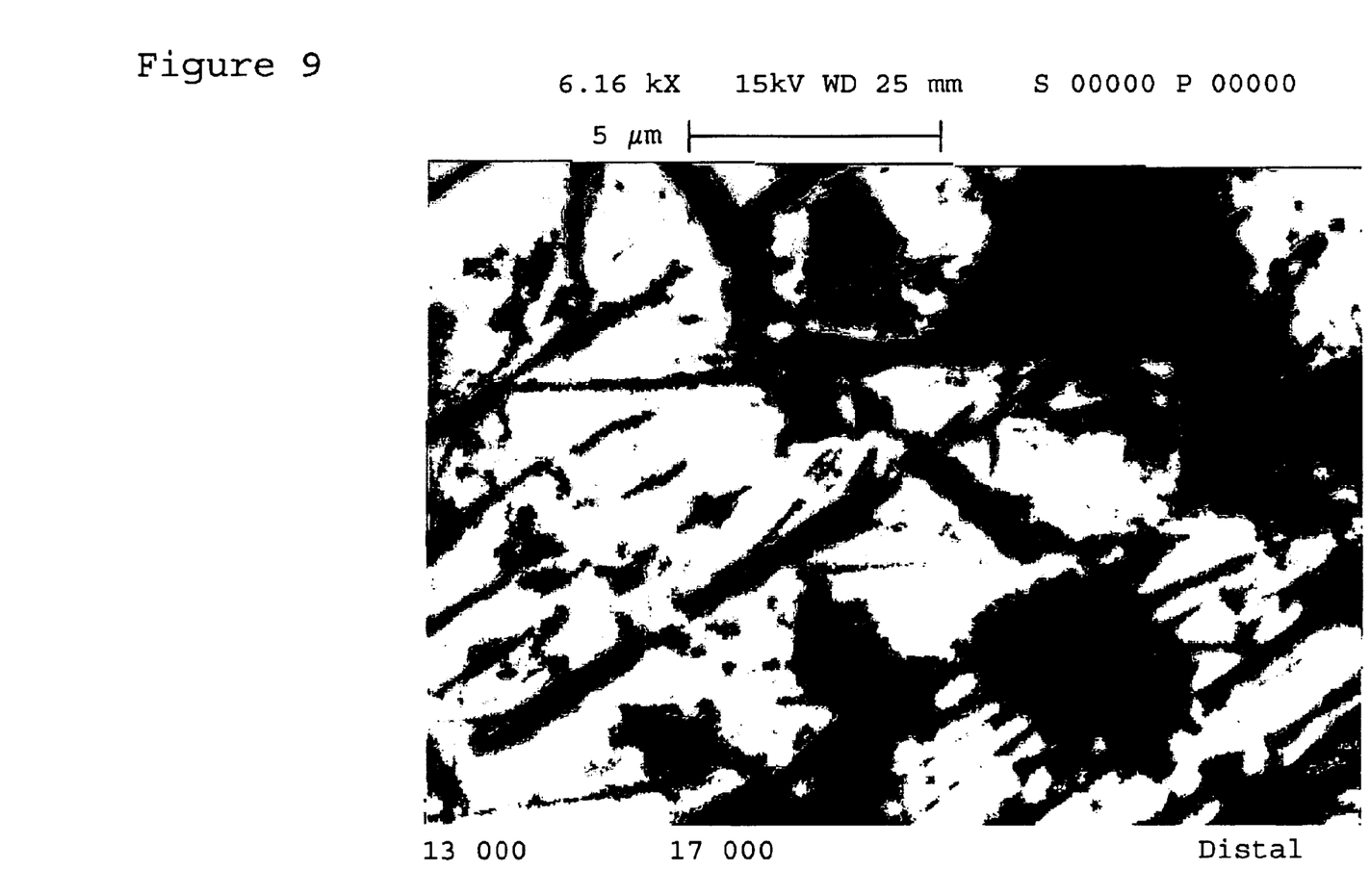
FIG. 9 shows an electron microscope photograph of the platinum surface of the ablation electrode of the non-treated ablation catheter from FIG. 10 with 6 160-fold magnification.

The electron microscope photographs illustrated in FIGS. 8 to 9 were obtained in order to provide proof of such behavior: they show that there is a catheter surface, sharp edged in the microstructure region, which has soft rounding and fewer sharp ridges or furrows after the mechanical treatment.

Figure 10:
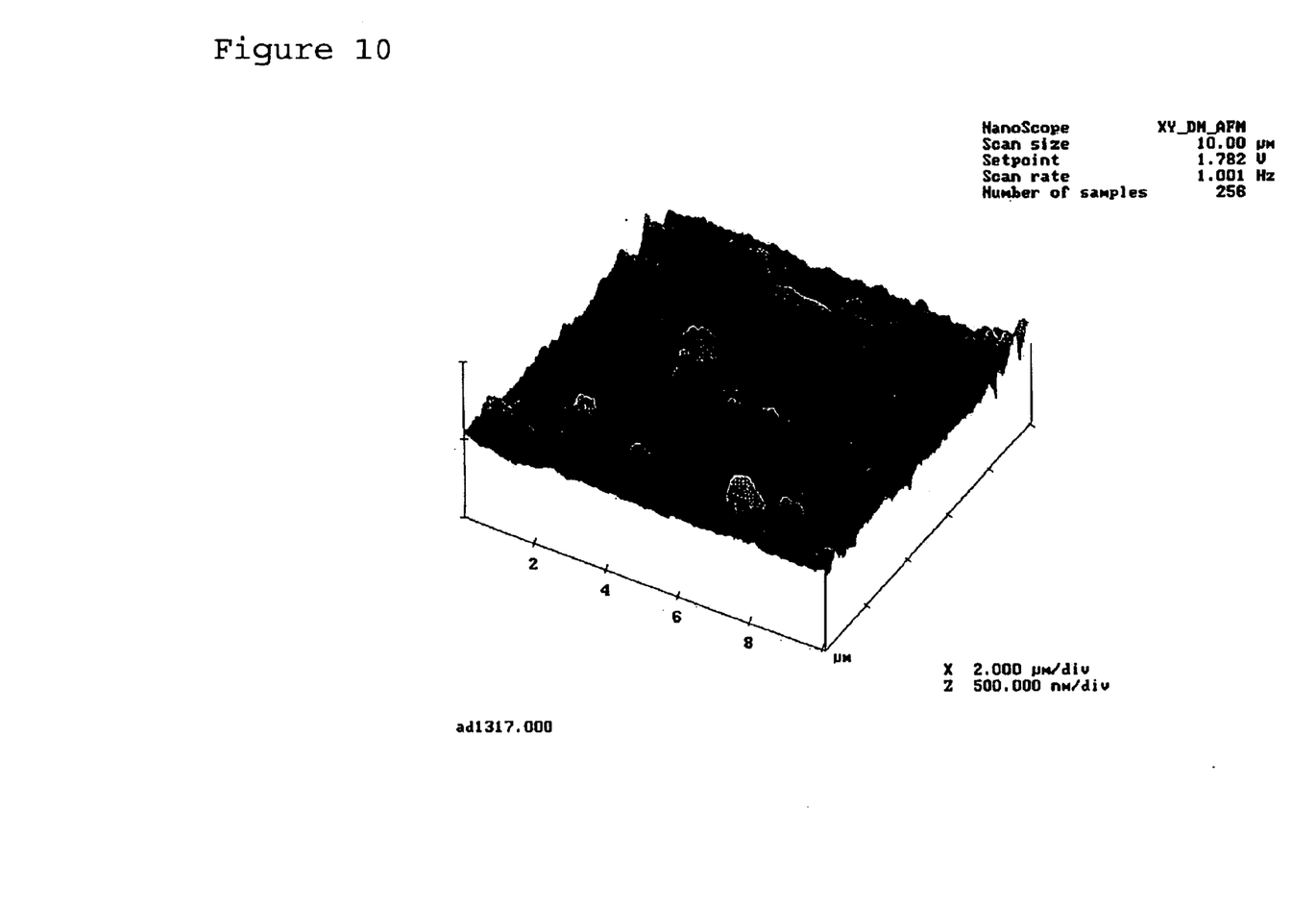
FIG. 10 shows an AFM (atomic force microscopic) or force microscopic plot of a surface region of size 10 times 10 $\mu$m of an untreated platinum ablation electrode.

Furthermore, the AFM (atomic force microscopic) or force microscopic plot of a surface of size 10 times 10 $\mu$m shows that electrical interference centers are also present on the surface of the at least one ablation or mapping electrode of the catheter 2 which has the shape of pins or needles and a diameter of less than 10 $\mu$m, in particular of less than 2 $\mu$m, the number and height of which are reduced by the method according to the invention.

The mechanical smoothing alone can reduce the mechanical friction of the ions on the surface, thus diminishing interference centers brought about thereby which are mechanically caused but electrically active.

It is assumed, furthermore, that elementary or amorphous platinum separated out from the metallic crystalline metal compound is also present owing to the mechanical treatment. The kinetic energy and/or the pure mechanical separating action of the grinding or polishing agent can lead to the detachment of platinum atoms from the metallic crystalline compound and their amorphous rearrangement.

A virtual detachment, that is to say a migration in the bound state of the platinum atom, also results in release of the atom from the crystal compound, and its rearrangement.

The rounded tips of the treated surface, which are exposed to increased attack, can also be explained thereby, the point being that attack from several sides can take place precisely in these regions.

This migration of platinum atoms can also compensate potentials present at the surface, for example at grain boundaries, or local field strength maxima at tips or sharp edges in such a way that even the effective electrical influence of such potentials or field strength maxima can be drastically reduced.

It is therefore possible to reduce not only the areal extent of the electrical interference centers present before the treatment, but also their electrical effect.

The inventors also found out that in many cases associated with a treated catheter structures of the surface of the ablation or mapping electrode no longer have sharp edges, that is to say very small radii of curvature. In a surface section with a length, width or height of less than 10 µm, the edges present had a radius of more than approximately 500 nm.

Sharper edges or smaller radii are either regularly reduced in number or no longer occur at all. In accordance with the invention, the radii of curvature of the edges occurring most are to be more than approximately 500 nm, preferably more than 100 nm, but at least more than 10 nm.

It may be pointed out that catheters treated according to the invention exhibit a clearly improved signal quality, that is to say substantially smaller interference signals, even without applied high-frequency energy. This improvement is not limited to ablation electrodes, but can also be used successfully in the case of mapping electrodes or mapping catheters.

What is claimed is:

1. Catheter for the ablation of biological, in particular of animal or human, tissue, including ablation of human myocardial tissue, said catheter comprising least one ablation or mapping electrode, wherein the at least one ablation or mapping electrode has a reduced number of electrical interference centers which generate microscopic electric field strength differences or microscopically different reaction capabilities and wherein the at least one ablation or mapping electrode has a treated surface with a microscopically smoothed surface structure whose microscopic edges or tips have a radius of curvature of more than 10 nm.

2. Catheter according to claim 1, characterized in that the electrical interference centers, are arranged to generate electric signals during the output of high-frequency energy to the at least one ablation or mapping electrode, and are essentially arranged on surface regions of the at least one ablation or mapping electrode, whereby the electrical interface centers are reduced in their number, areal extent or electrical effect.

3. Catheter according claim 1, characterized in that the at least one ablation or mapping electrode has a mechanically treated surface.

4. Catheter according to claim 1, characterized in that structures of the surface of the at least one ablation or mapping electrode have a rounded surface structure whose edges or tips have a radius of curvature of more than approximately 500 nm.

5. Catheter according to claim 1, characterized in that the at least one ablation or mapping electrode comprises a noble metal.

6. Catheter according to claim 5, wherein the noble metal comprises platinum.

7. Catheter according to claim 1, characterized in that the ablation or mapping electrode comprises a lapped or polished surface.

8. Catheter according to claim 1, characterized in that the ablation or mapping electrode comprises a rolled surface.

9. Catheter according to claim 1, wherein the radius of curvature of the microscopic edges or tips are more than 100 nm.

10. Method for producing a catheter with improved electrical properties, the method comprising the following steps:

providing a catheter which comprises at least one ablation or mapping electrode, and treating the at least one ablation or mapping electrode on its surface, wherein the surface of the at least one ablation or mapping electrode is smoothed at least until structures which have a diameter of less than 10 µm are reduced in number.

11. Method for producing a catheter according to claim 10, in which the surface of the at least one ablation or mapping electrode of the catheter is at least one of ground, lapped and polished.

12. Method for producing a catheter according claim 10, in which the surface of the at least one ablation or mapping electrode of the catheter is rolled with a smooth roller.

13. Method for producing a catheter according to claim 10, in which the surface of the at least one ablation or mapping electrode of the catheter is treated with a soft grinding or polishing agent which comprises a carbonate.

14. Method according to claim 13, wherein the soft grinding or polishing agent comprises an alkali or alkaline earth carbonate, in particular calcium carbonate.

15. Method for producing a catheter according to claim 10, in which structures on the surface of the at least one ablation or mapping electrode of the catheter which have radii of curvature of more than approximately 500 nm, are reduced in number.

16. Method for producing a catheter according to claim 10, in which structures on the surface of the at least one ablation or mapping electrode of the catheter which are shaped like pins or needles and have a diameter of less than 10 µm are reduced in number.

17. Method for producing a catheter according to claim 10, in which the mechanical processing comprises the application of a film with a smooth surface, in particular the grinding of the film with a smooth surface onto the at least one ablation or mapping electrode.

18. Method according to claim 10, wherein the radius of curvature of the structures is more than 100 nm.

* * * * *